(12) United States Patent
Smith

(10) Patent No.: US 8,747,334 B1
(45) Date of Patent: Jun. 10, 2014

(54) METHOD FOR SPECIMEN SAMPLE COLLECTION

(76) Inventor: Jack V. Smith, Arden, NC (US)

(*) Notice: Subject to any disclaimer, the term of this patent is extended or adjusted under 35 U.S.C. 154(b) by 365 days.

(21) Appl. No.: 13/307,659

(22) Filed: Nov. 30, 2011

(51) Int. Cl.
*A61B 5/00* (2006.01)
*B65D 81/00* (2006.01)

(52) U.S. Cl.
USPC .......................................... 600/573

(58) Field of Classification Search
USPC ........... 600/573, 575; 210/474; 141/237, 242; 206/569; 220/86.1; 422/278
See application file for complete search history.

(56) References Cited

U.S. PATENT DOCUMENTS

| | | | |
|---|---|---|---|
| 4,768,238 A | | 9/1988 | Kleinberg et al. |
| 4,771,486 A | | 9/1988 | Gutierrez et al. |
| 5,837,139 A | * | 11/1998 | Lerch .......................... 210/474 |
| 2005/0096563 A1 | | 5/2005 | Liang |
| 2010/0288059 A1 | | 11/2010 | Viljoen et al. |

* cited by examiner

*Primary Examiner* — Brian Szmal
(74) *Attorney, Agent, or Firm* — Michele L. Lawson; Smith & Hopen, P.A.

(57) ABSTRACT

A method of collecting a specimen sample and simultaneously dividing the sample into separate portions is presented. The method of the instant invention is comprised of providing a specimen collector comprised of a collection receptacle attached by a connector to at least 2 tubes which lead to at least 2 conduits which in turn empty into separate collection containers; expelling a biological specimen into the collection receptacle of the specimen collection device; and allowing the biological specimen to flow downward through the device and into separate specimen containers.

13 Claims, 6 Drawing Sheets

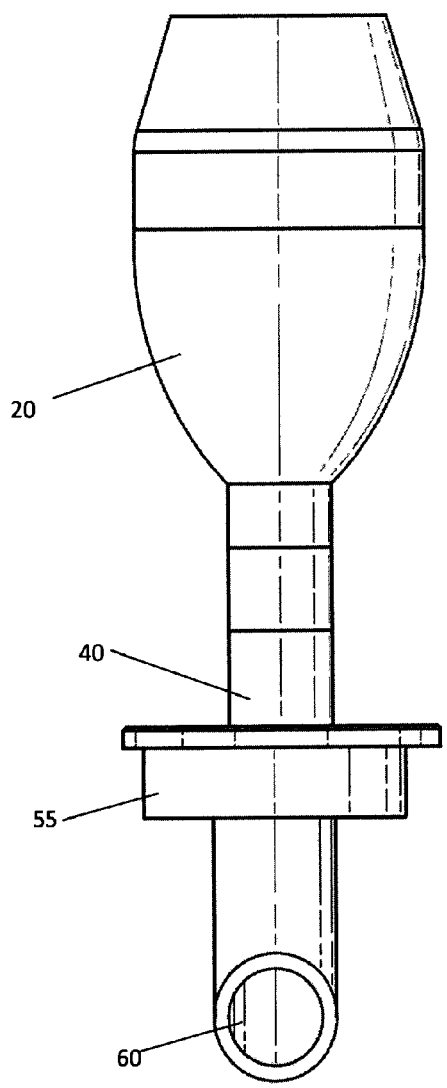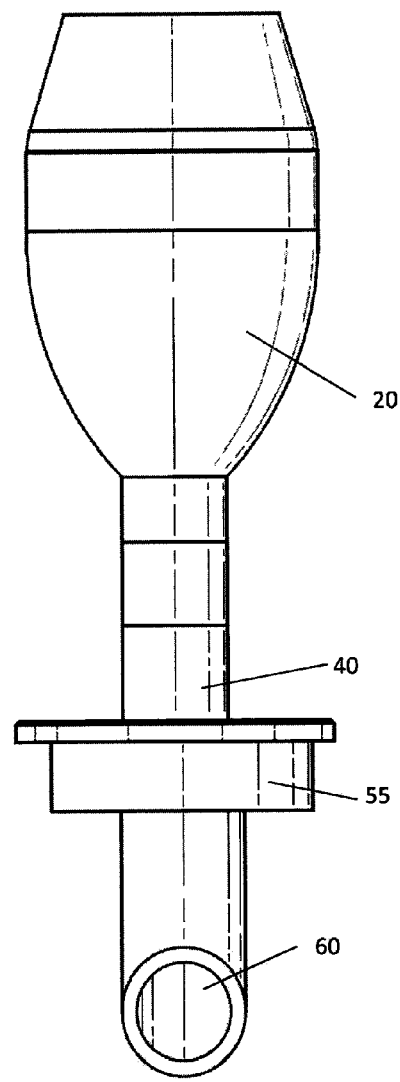
FIG. 5
FIG. 6

METHOD FOR SPECIMEN SAMPLE COLLECTION

FIELD OF INVENTION

This invention relates to methods of collecting specimens. Specifically, the invention provides a method for specimen collection in which the same sample is simultaneously divided into separate portions.

BACKGROUND OF THE INVENTION

The unstimulated saliva production of a healthy adult can range from about 0.08 ml/min to about 1.85 ml/min with the average being about 0.3 ml/min. Stimulation, through either gustatory or masticatory means, may increase the rate of saliva production between about 3 to about 6 fold.

There are many techniques for the collection of an oral fluid such as saliva for analysis. For example, a device may be placed in the mouth of a subject and saliva obtained through vacuuming, absorption, and aspiration. Alternatively, an oral fluid expectoration method may be used in which the subject expectorates saliva into a collection container.

The collection and analysis of a biological fluid, such as saliva, is performed for a variety of reasons ranging from diagnosis of disease to detection of drugs or other substances. In some cases, the fragility or hazardous nature of the sample requires that the sample is tested or preserved immediately. Many clinical situations require a sample of a collected specimen to be isolated for use. In many cases, multiple different tests must be performed on the sample which may require the sample to be divided into separate portions. Separate portions may also be needed in the case of storage for future testing or shipping to a centralized laboratory.

In the prior art, if different portions of a sample were required for testing purposes, the subject would either have to give a new sample, which may be difficult for some patients, or the sample that was obtained would have to be separated into different portions by a technician. Separating the sample into different portions would pose a risk to the technician who handles the specimen since separating the sample would generally entail opening the specimen container and pouring or extracting portions of the sample to be placed into separate containers. This practice runs the risk of contamination of the sample as well as the risk of exposing the technician to any disease contained within the sample. In addition, during transfer of the sample into separate portions, the specimen samples may degrade or be damaged which will affect the integrity of the test results.

Given the shortcomings of the prior art, what is needed is a method of obtaining separate portions of the same sample without the risk of contamination and exposure that is experienced in the prior art.

SUMMARY OF INVENTION

The present invention meets the heretofore unfulfilled need of obtaining separate portions of the same sample without the risk of contamination and exposure. What is presented is a method of collecting a biological specimen which allows the subject to provide one sample into a collection receptacle that is divided into separate portions immediately.

In an embodiment, a method of collecting a specimen sample and dividing it into separate portions is presented comprising: (a) providing a specimen collector comprising a collection receptacle having a first and a second end wherein the second end is divided into at least 2 chambers; at least 2 tubes having a first and a second end wherein the first end of each tube is attached to each chamber; wherein the second end of each tube is positioned above or within a separate specimen container; (b) expelling a bodily fluid into the collection receptacle; and (c) allowing the bodily fluid to flow through the specimen collector and into the separate specimen containers. The bodily fluid may be saliva. The collection receptacle may be essentially circular in shape.

In another embodiment, a method of collecting a specimen sample and dividing it into separate portions is presented comprising: (a) providing a specimen collector comprising a collection receptacle having a top and a bottom portion wherein the top portion is open and the bottom portion of the receptacle is angled inward; a connector attached to the bottom portion of the collection receptacle wherein the connector is divided into at least two chambers; at least two tubes having a first end and a second end wherein the first end of a first tube is fluidly connected to a first chamber and the first end of a second tube is fluidly connected to a second chamber; at least two conduits having a first end and a second end wherein the second end of the first tube is positioned within the first end of a first conduit and the second end of the second tube is positioned within the first end of a second conduit; and wherein the second end of each conduit is positioned above or within a separate specimen cup; (b) expelling a bodily fluid into the collection receptacle; and (c) allowing the bodily fluid to flow through the specimen collector and into the separate specimen containers.

The specimen collector may be further comprised of a base having a top and a bottom surface wherein the first ends of the at least two conduits are attached to the bottom surface of the base and the second ends of the at least two tubes extend through the top surface of the base into the at least two conduits. The at least two conduits may have a larger diameter than diameter of the at least two tubes. The second end of the at least two conduits may be angled. The specimen collected may be saliva. The collection receptacle may be essentially circular in shape.

In a further embodiment, a method of collecting a specimen sample and dividing it into separate portions is presented comprising: (a) providing a specimen collector comprising a collection receptacle having a top and a bottom portion wherein the bottom portion of the receptacle is angled inward; a connector attached to the bottom portion of the collection receptacle wherein the connector is divided into at least two chambers; at least two tubes having a first end and a second end wherein the first end of a first tube is fluidly connected to a first chamber and the first end of a second tube is fluidly connected to a second chamber; a base having a top and a bottom surface wherein the at least two tubes extend though the top surface of the base; first ends of the at least two conduits are attached to the bottom surface of the base and the second ends of the at least two tubes extend through the top surface of the base into the at least two conduits; at least two conduits having a first end and a second end wherein the first end of the at least two conduits are attached to the bottom surface of the base and the second ends of the at least two tubes extend into the at least two conduits; and wherein the second end of each conduit is positioned above or within a separate specimen container; (b) expelling a bodily fluid into the collection receptacle; and (c) allowing the bodily fluid to flow downward through the collection receptacle, the tubes, the conduits and finally into the separate specimen containers.

The bodily fluid may be saliva. The at least two conduits may have a larger diameter than diameter of the at least two tubes. The second end of the at least two conduits may be angled. The collection receptacle may be essentially circular in shape.

BRIEF DESCRIPTION OF THE DRAWINGS

For a fuller understanding of the invention, reference should be made to the following detailed description, taken in connection with the accompanying drawings, in which:

FIG. 5 is a first side view of the specimen collector.
FIG. 6 is a second side view of the specimen collector.

DETAILED DESCRIPTION OF THE PREFERRED EMBODIMENT

Figure 1:
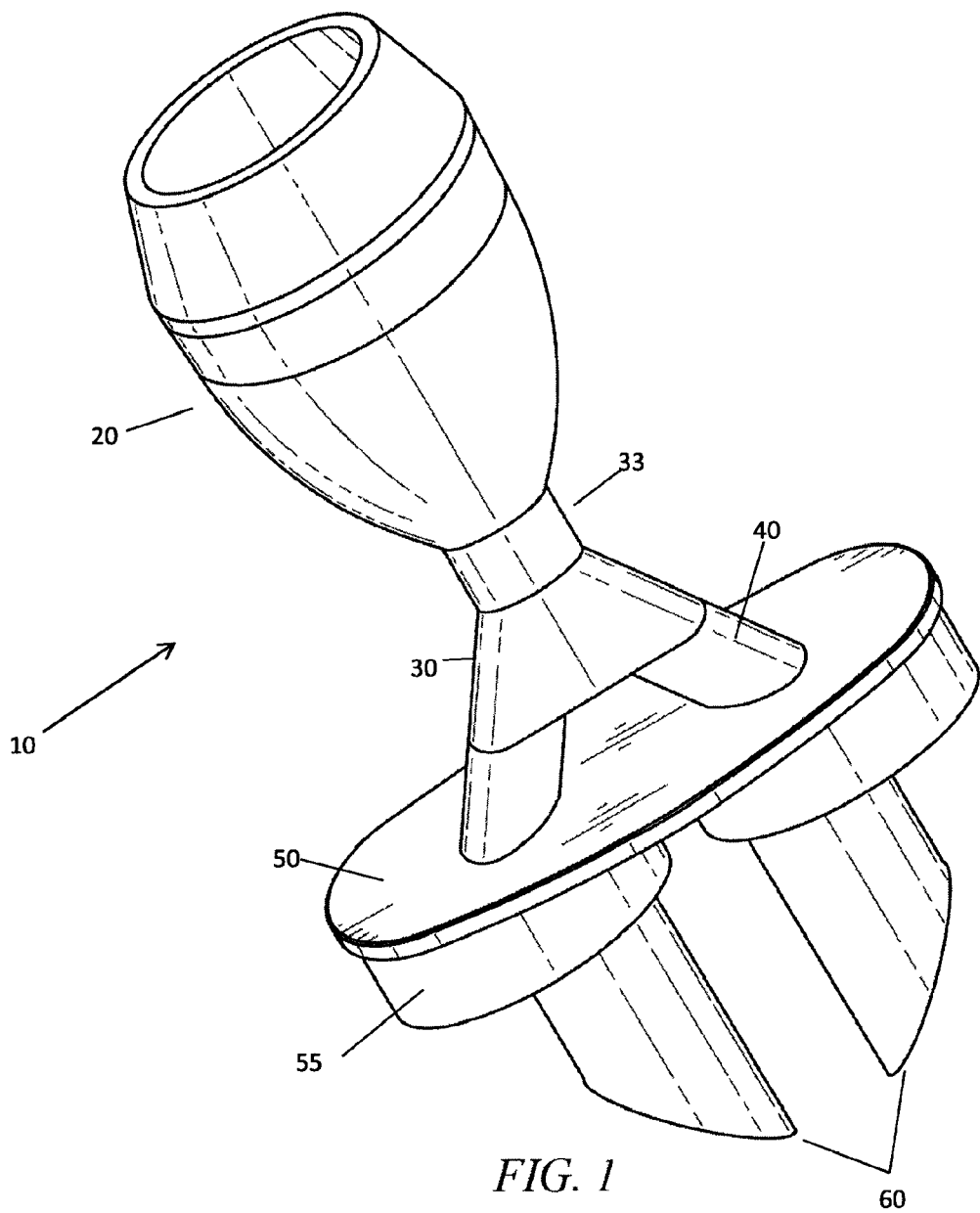
FIG. 1 is a perspective view of the specimen collector.
Figure 2:
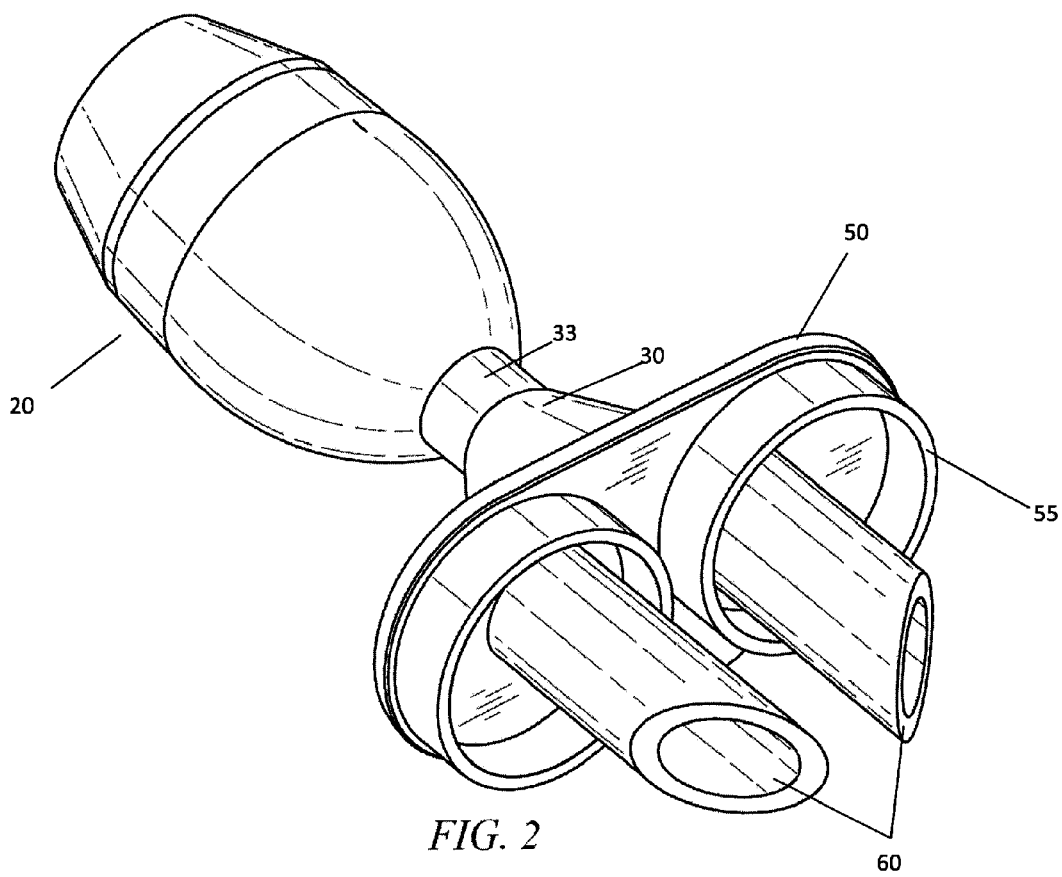
FIG. 2 is a bottom perspective view of the specimen collector.
Figure 3:
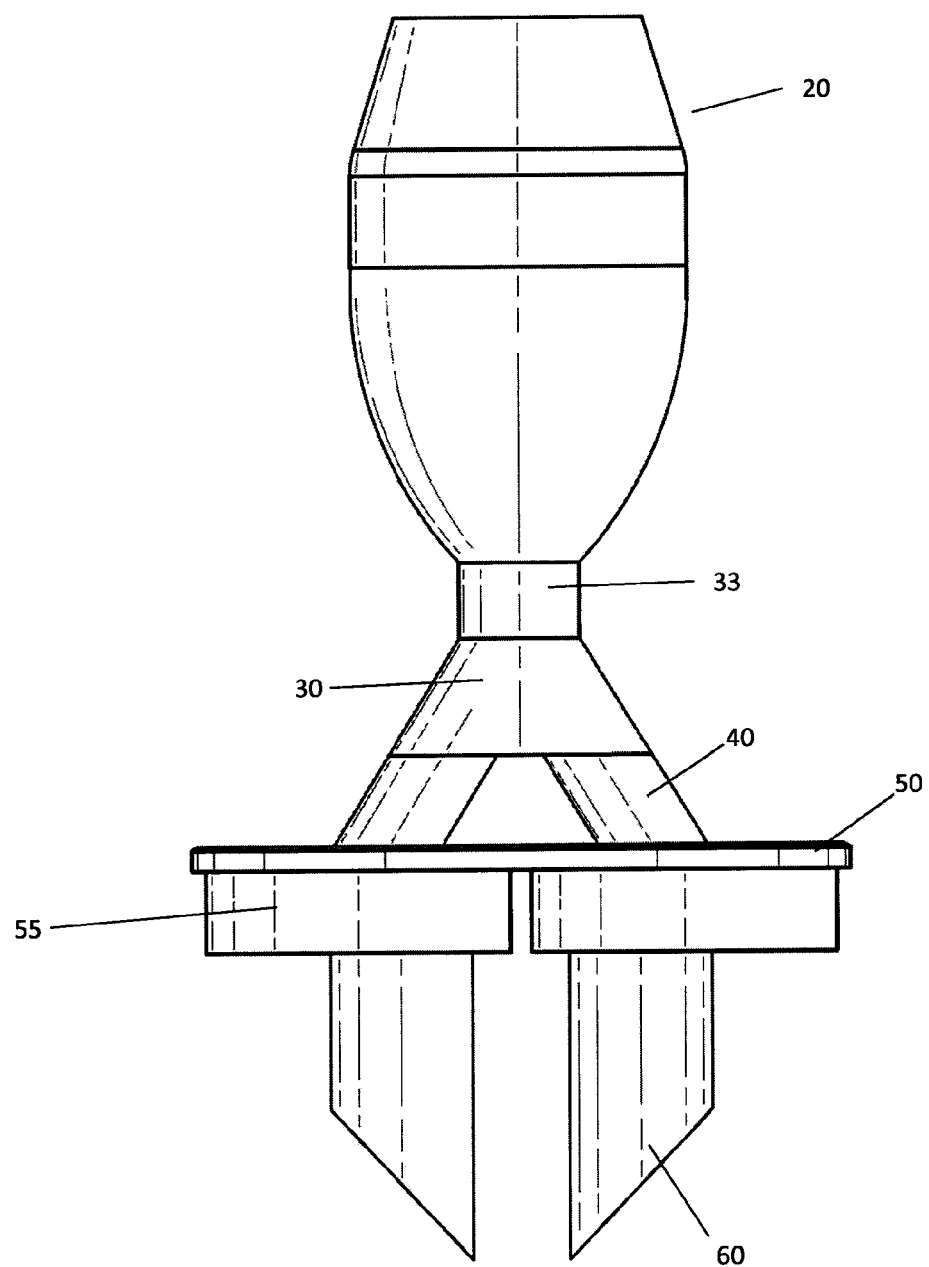
FIG. 3 is a front view of the specimen collector.
Figure 4:
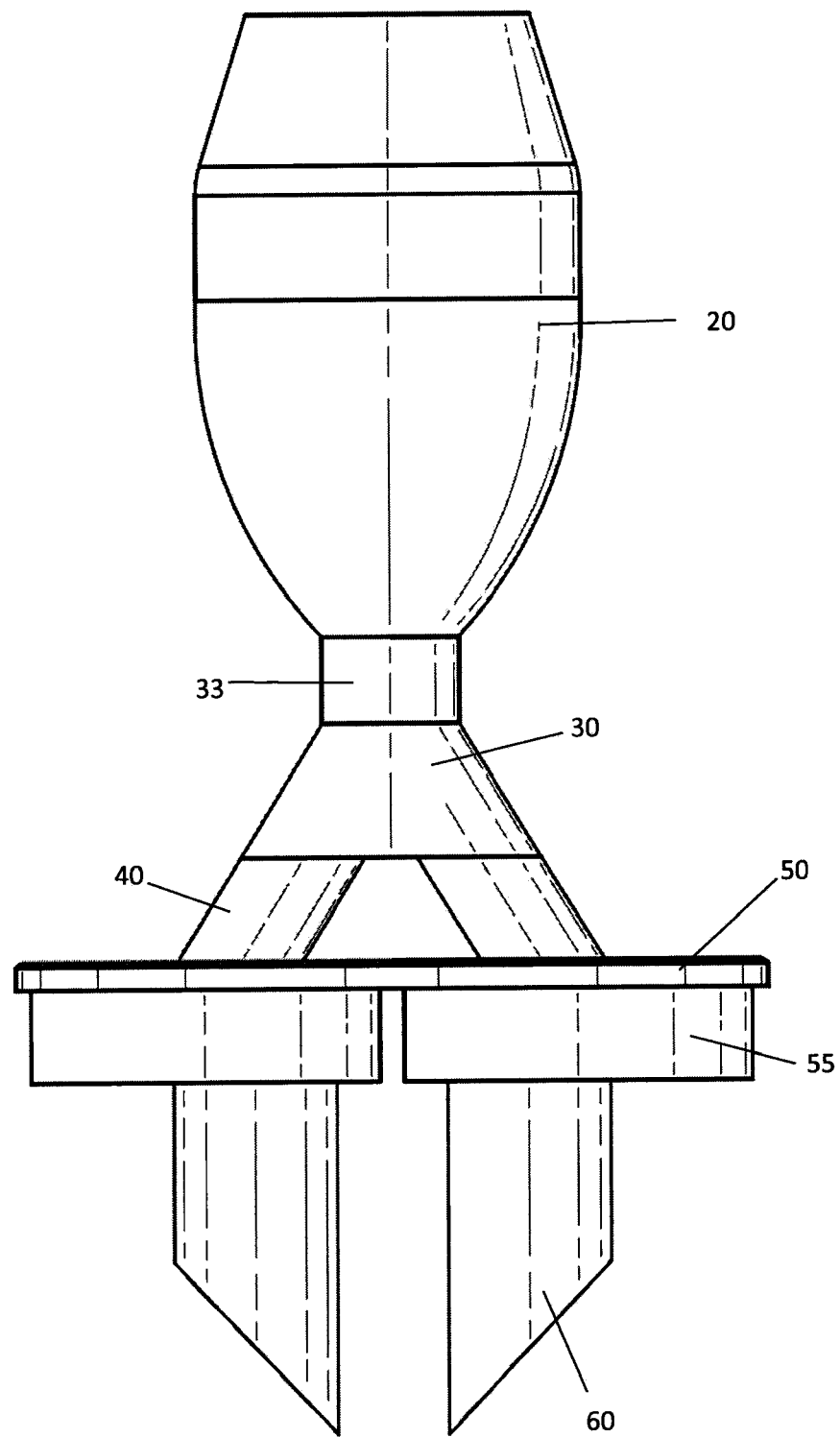
FIG. 4 is a back view of the specimen collector.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

The present invention comprises a method for collecting a biological specimen sample from a subject while simultaneously separating the sample into different portions. The different portions of the biological specimen may be used for further medical testing, including diagnostic testing, as well as for forensic testing and other types of testing or for storage or transport.

Generally a method of collecting a specimen sample and dividing it into separate portions is presented comprising: (a) providing a specimen collector comprising a collection receptacle having a first and a second end wherein the second end is divided into at least 2 chambers; at least 2 tubes having a first and a second end wherein the first end of each tube is attached to each chamber; wherein the second end of each tube is positioned above or within a separate specimen container; (b) expelling a bodily fluid into the collection receptacle; and (c) allowing the bodily fluid to flow through the specimen collector and into the separate specimen containers.

Referring to FIGS. 1-8, a specimen collector having the ability to simultaneously divide a single specimen sample into two or more separate specimen samples is presented. Specimen collector 10 of the present invention generally comprises a collection receptacle 20, a connector 30 divided into at least 2 separate chambers 35, at least 2 tubes 40, and at least 2 conduits 60. In an embodiment, specimen collector 10 may also be comprised of a base 50.

Referring to FIGS. 1-6, collection receptacle 20 may be generally an elongated bowl-shaped structure having open first and second ends. In an embodiment, collection receptacle 20 may be essentially circular in shape and be wider at the top than at the bottom. While collection receptacle 20 is described as being essentially circular in shape, it can also be constructed in other shapes without deviating from the spirit of invention. The bottom of collection receptacle 20 may be angled inward to facilitate the movement of the bodily fluid through collection receptacle 20 and eventually into specimen containers. Collection receptacle 20 is preferably constructed of a hydrophobic material including, but not limited to, glass, metal, rubber or plastic.

Figure 7:
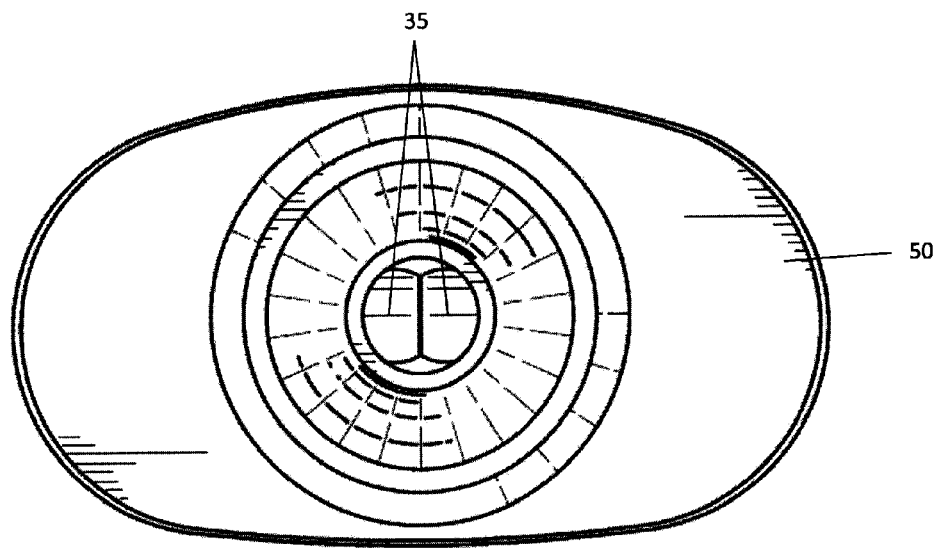
FIG. 7 is a top view of the specimen collector.
Figure 8:
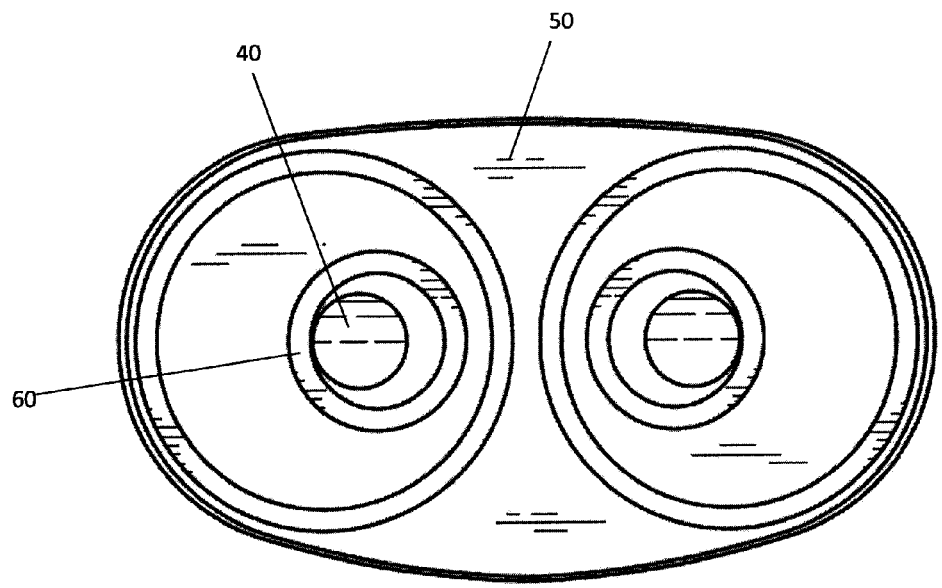
FIG. 8 is a bottom view of the specimen collector.

In an embodiment, the bottom of collection receptacle 20 may be attached to a first end of connector 30. Connector 30 may have a collar 33 which connects to the bottom of collection receptacle 20. The interior of connector 30 is hollow and may be divided into at least two chambers 35 as depicted in FIG. 7. Chambers 35 have a first and a second end. Chambers 35 extend at least through the length of the second end of connector 30. The second end of each chamber 35 is in fluid communication with tube 40.

Tube 40 may extend from chamber 35 outwardly at a slight angle. As there are at least 2 chambers 35, similarly there are at least 2 tubes 40, each of which corresponds to a separate chamber 35. Tube 40 is hollow and is comprised of a first end and a second end with the first end extending from chamber 35. Tube 40 is generally cylindrical in shape and may be flexible or rigid. Tube 40 may be constructed of the same material as collection receptacle 20 or may be constructed of a more flexible material.

In an embodiment, second end of tube 40 is connected to base 50. Base 50 can be constructed of the same material as collection receptacle 20 and is preferably rigid. Base 50 has a top surface and a bottom surface. Base 50 may be elongated in shape being longer than it is wide and may be constructed in any shape, including but not limited to circular, oval, rectangular and square. Base 50 preferably has rounded edges. The bottom surface of base 50 may contain at least 2 flanges 55. In an embodiment where base 50 is not used, tubes 40 extend directly to conduits 60 and are affixed thereto so that the flow of saliva is permitted unhindered through tubes 40 and into conduits 60.

At least 2 conduits 60 are fixedly attached to the bottom surface of base 50. In an embodiment, each conduit 60 is attached at each flange 55. Conduits 60 are generally hollow cylindrical structures having a first and a second end where the first end is attached to the bottom surface of base 50. The second end of conduit 60 may be angled to facilitate flow of the bodily fluid into a specimen container. Conduits 60 preferably have a diameter that is larger than that of tubes 40. The second end of tubes 40 may be positioned within conduits 60 to facilitate the flow of the biological fluid through tubes 40 and into conduits 60. Alternatively, tubes 40 may be affixed to conduits 60 in which case tubes 40 may have the same diameter as conduits 60. Each conduit 60 empties into a separate specimen container. Conduit 60 may be positioned so that its second end is contained within or above the opening in specimen container. (not shown) Alternatively, the second end of conduit 60 may be adapted with female or male threads and a specimen container having corresponding threads may be removably attached to conduit 60. (not shown)

In use as a method of collecting a biological sample and simultaneously dividing it into separate portions, a user would deposit or expel the biological fluid to be analyzed into collection receptacle 20. For example, if saliva is collected then a user would expectorate their saliva into collection receptacle 20. The saliva would travel through collection receptacle 20 into connector 30 and through at least one chamber 35. Once the saliva is through the at least one chamber 35, it will travel through tube 40 and subsequently conduit 60. The saliva travels through conduit 60 and is expelled into a specimen container.

Given the separate chambers 35, any bodily fluid, such as saliva, that is deposited into collection receptacle 20 may flow through one or more of chambers 35. Each chamber 35 is attached to a corresponding tube 40 which in turn is attached to a corresponding conduit 60. Each conduit 60 is positioned at a separate specimen container. By allowing the same bodily fluid sample to flow through separate channels (i.e. through separate corresponding chambers, tubes and conduits), the same bodily fluid sample may fill two or more separate specimen containers at the same time and thus the same bodily fluid sample may be divided into two or more samples for analysis.

Specimen collector device 10 may be constructed of a hydrophobic rigid or semi-rigid material may be used to construct specimen collector device 10. For example, a material such as glass or metal or a hydrophobic polymeric material such as a plastic or rubber material may be used. Other materials that may be used to construct specimen collector device 10 are well known by those of ordinary skill in the art.

The components of specimen collector device 10 may be formed as a single molded unit or alternatively the separate components may be attached together as noted above.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween. Now that the invention has been described.

What is claimed is:

1. A method of collecting a specimen sample and dividing it into separate portions comprising:
    a) providing a specimen collector comprising
        a collection receptacle having a first and a second end wherein the second end is divided into at least two chambers;
        at least two tubes having a first and a second end wherein the first end of each tube is attached to each chamber;
        at least two conduits having a first end and a second end wherein the second end of a first tube is positioned within the first end of a first conduit and the second end of a second tube is positioned within the first end of a second conduit;
        a base having a top and a bottom surface wherein the first ends of the at least two conduits are attached to the bottom surface of the base and the second ends of the at least two tubes extend through the top surface of the base into the at least two conduits;
        wherein the second end of each tube is positioned above or within a separate specimen container;
    b) expelling a bodily fluid into the collection receptacle; and
    c) allowing the bodily fluid to flow through the specimen collector and into the separate specimen containers.

2. The method of claim 1, wherein the bodily fluid is saliva.

3. The method of claim 1, wherein the collection receptacle is circular in shape.

4. A method of collecting a specimen sample and dividing it into separate portions comprising:
    a) providing a specimen collector comprising
        a collection receptacle having a top and a bottom portion wherein the top portion is open;
        a connector attached to the bottom portion of the collection receptacle wherein the connector is divided into at least two chambers;
        at least two tubes having a first end and a second end wherein the first end of a first tube is fluidly connected to a first chamber and the first end of a second tube is fluidly connected to a second chamber;
        at least two conduits having a first end and a second end wherein the second end of the first tube is positioned within the first end of a first conduit and the second end of the second tube is positioned within the first end of a second conduit;
        a base having a top and a bottom surface wherein the first ends of the at least two conduits are attached to the bottom surface of the base and the second ends of the at least two tubes extend through the top surface of the base into the at least two conduits; and
        wherein the second end of each conduit is positioned above or within a separate specimen cup;
    b) expelling a bodily fluid into the collection receptacle; and
    c) allowing the bodily fluid to flow through the specimen collector and into the separate specimen containers.

5. The method of claim 4, wherein the at least two conduits have a larger diameter than diameter of the at least two tubes.

6. The method of claim 4, wherein the second end of the at least two conduits are angled.

7. The method of claim 4, wherein the specimen collected is saliva.

8. The method of claim 4, wherein the collection receptacle is circular in shape.

9. A method of collecting a specimen sample and dividing it into separate portions comprising:
    a) providing a specimen collector comprising
        a collection receptacle having a top and a bottom portion wherein the bottom portion of the receptacle is angled inward;
        a connector attached to the bottom portion of the collection receptacle wherein the connector is divided into at least two chambers;
        at least two tubes having a first end and a second end wherein the first end of a first tube is fluidly connected to a first chamber and the first end of a second tube is fluidly connected to a second chamber;
        a base having a top and a bottom surface wherein the at least two tubes extend though the top surface of the base;
        at least two conduits having a first end and a second end wherein the first end of the at least two conduits are attached to the bottom surface of the base and the second ends of the at least two tubes extend into the at least two conduits; and
        wherein the second end of each conduit is positioned above or within a separate specimen container;
    b) expelling a bodily fluid into the collection receptacle; and
    c) allowing the bodily fluid to flow downward through the collection receptacle, the tubes, the conduits and finally into the separate specimen containers.

10. The method of claim 9, wherein the bodily fluid is saliva.

11. The method of claim 9, wherein the at least two conduits have a larger diameter than diameter of the at least two tubes.

12. The method of claim 9, wherein the second end of the at least two conduits are angled.

13. The method of claim 9, wherein the collection receptacle is circular in shape.

* * * * *